(12) United States Patent
Trieu

(10) Patent No.: US 9,678,078 B2
(45) Date of Patent: *Jun. 13, 2017

(54) METHODS AND COMPOSITIONS FOR PERSONALIZED MEDICINE BY POINT-OF-CARE DEVICES FOR BRAIN NATRIURETIC PEPTIDE

(71) Applicant: Autotelic LLC, Fountain Valley, CA (US)

(72) Inventor: Vuong Trieu, Agoura Hills, CA (US)

(73) Assignee: Autotelic LLC, City of Industry, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/526,376

(22) Filed: Oct. 28, 2014

(65) Prior Publication Data

US 2015/0147823 A1 May 28, 2015

Related U.S. Application Data

(63) Continuation-in-part of application No. PCT/US2013/046040, filed on Jun. 15, 2013.

(60) Provisional application No. 61/961,969, filed on Oct. 28, 2013, provisional application No. 61/659,981, filed on Jun. 15, 2012, provisional application No. 61/667,081, filed on Jul. 2, 2012, provisional application No. 61/671,717, filed on Jul. 14, 2012.

(51) Int. Cl.
*G01N 33/574* (2006.01)

(52) U.S. Cl.
CPC ... *G01N 33/57449* (2013.01); *G01N 2333/58* (2013.01)

(58) Field of Classification Search
CPC ............... G01N 33/57449; G01N 2333/58
See application file for complete search history.

(56) References Cited

U.S. PATENT DOCUMENTS

2004/0096363 A1* 5/2004 Porter .................... 422/68.1
2009/0042224 A1* 2/2009 Hellstrom et al. ........... 435/7.92

FOREIGN PATENT DOCUMENTS

WO 2011/017077 A2 2/2011
WO 2013/188860 A1 12/2013

OTHER PUBLICATIONS

Gerbes et al., Transcription of Brain Natriuretic Peptide and Atrial Natriuretic Peptide Genes in Human Tissues, Journal of Clinical Endocrinology and Metabolism, 78(6):1307-1311, 1994.*
Silver et al., BNP consensus Panel 2004: A Clinical Approach for the Diagnostic, Prognostic, Screening, Treatment Monitoring, and Therapeutic roles of Natriuretic Peptides in Cardiovascular diseases, Congestive Heart Failure, 10(5), 2004, total of 36 pages.*
International Preliminary Report on Patentability, issued Dec. 16, 2014, in International Application No. PCT/US2013/046040, filed Jun. 15, 2013, 7 pages.
International Search Report, mailed Sep. 2, 2013, issued in International Application No. PCT/US2013/046040, filed Jun. 15, 2013, 4 pages.
Petrik, J., "Diagnostic Applications of Microarrays," Transfusion Medicine 16(4):233-247, Aug. 2006.
Suh, S.K, et al., "Ovarian Cancer Biomarkers for Molecular Biosensors and Translational Medicine," Expert Review of Molecular Diagnostics 10(8):1069-1083, Nov. 2010.
Wang, S., et al., "Integration of Cell Phone Imaging With Microchip ELISA to Detect Ovarian Cancer HE4 Biomarker in Urine at the Point-of-Care," Lab on a Chip 20(11):3411-3418, Oct. 2011. (Author manuscript Pmcid: PMC3767574, available in PMC Sep. 9, 2013, 16 pages).
Warsinke, A., "Point-of-Care Testing of Proteins," Analytical and Bioanalytical Chemistry 393(5):1393-1405, Mar. 2009.

* cited by examiner

*Primary Examiner* — Andrea S Grossman
(74) *Attorney, Agent, or Firm* — Christensen O'Connor Johnson Kindness PLLC

(57) ABSTRACT

Methods, devices, reagent, systems and kits for the detection, diagnosis of ovarian cancer as well as for the monitoring of ovarian cancer progression and for monitoring the progress of ovarian cancer treatments using BNP as a biomarker.

1 Claim, 6 Drawing Sheets

METHODS AND COMPOSITIONS FOR PERSONALIZED MEDICINE BY POINT-OF-CARE DEVICES FOR BRAIN NATRIURETIC PEPTIDE

CROSS-REFERENCES TO RELATED APPLICATIONS

This application claims the benefit of U.S. Provisional Application No. 61/961,969, filed Oct. 28, 2013, and is a continuation-in-part of PCT/US2013/046040, filed Jun. 15, 2013, which claims the benefit of U.S. Provisional Application No. 61/659,981, filed Jun. 15, 2012; U.S. Provisional Application No. 61/667,081, filed Jul. 2, 2012; and U.S. Provisional Application No. 61/671,717, filed Jul. 14, 2012, each expressly incorporated herein by reference in its entirety.

FIELD OF THE INVENTION

The present invention relates to methods, devices, reagent, systems and kits for the detection, diagnosis of ovarian cancer as well as for the monitoring of ovarian cancer progression and for monitoring the progress of various cancer treatments including ovarian cancer. The present invention also relates to point-of-care testing (POCT) and methods for determining concentrations of brain natriuretic peptide (BNP) in a subject.

BACKGROUND OF THE INVENTION

Cancer is a leading cause of death worldwide, accounting for 7.6 million deaths (around 13% of all deaths) in 2008. Ovarian cancer is the ninth most common cancer in women and the fifth leading cause of cancer-related deaths in women in the US. One of every 72 women will develop ovarian cancer and one of every 100 will die from this form of cancer. The American Cancer Society estimates that in 2013, 22,240 women will be diagnosed with ovarian cancer and about 14,230 will die from ovarian cancer. About 85% to 90% of ovarian cancers are epithelial ovarian carcinomas.

Treatment options include surgery, chemotherapy, and occasionally radiation therapy. Surgery usually involves the removal of one or both ovaries, fallopian tubes and the uterus. In advanced disease, surgically removing all abdominal metastases enhances the effect of chemotherapy and helps improve survival. For women with stage III ovarian cancer in which removal of cancerous tissue has been performed, studies show that chemotherapy administered both intravenously and directly into the peritoneal cavity improves survival.

The identification of tumor markers suitable for early detection and diagnosis of cancer and in particular, ovarian cancer would improve the clinical outcome of patients, especially those presenting vague or no symptoms. Presently no cost effective screening tests have been developed.

Ovarian epithelial cancer is more common in individuals with elevated gonadotropin-releasing hormone (GnRH) including follicle-stimulating hormone (FSH) and luteinizing hormone (LH), such as postmenopausal women or women who have received treatment to induce ovulation. Conversely, reduced risk of ovarian cancer is associated with a history of multiple pregnancies, breastfeeding, oral contraceptive use, and estrogen replacement therapy, all of which are related to lower levels of and reduced exposure to FSH and LH. FSH, follicle stimulating hormone, regulates gene expression in ovarian tumors (Chu S, Rushdi S, Zumpe E T, Mamers P, Healy D L, Jobling T, Burger H G, Fuller P J. (2002) FSH-regulated gene expression profiles in ovarian tumors and normal ovaries. *Mol Hum Reprod.* 8:426-33) and causes neovascularization of ovarian cancers by increasing vascular endothelial growth factor (VEGF) expression through upregulation of surviving (Huang Y, Hua K, Zhou X, Jin H, Chen X, Lu X, Yu Y, Zha X, Feng Y. (2008) Activation of the PI3K/AKT pathway mediates FSH-stimulated VEGF expression in ovarian serous cystadenocarcinoma. *Cell Res.* 18:780-91).

Currently, cancer antigen 125 (CA-125) is used as a serum biomarker for ovarian cancer. Serum concentrations of CA-125 are elevated in 75-80% of patients with advanced-stage disease and this marker. CA125 is used as a serum tumor marker for monitoring response to chemotherapy, detecting disease recurrence, as well as distinguishing malignant from benign pelvic masses. However, it is presently not an appropriate diagnostic biomarker as the majority of healthy women with high levels of CA-125 do not have cancer.

Accordingly, there is a need for improved methods of detection and diagnosis of cancer including ovarian cancer as well as methods for monitoring the progress of the disease and monitoring the progress of various treatments for ovarian cancer including point of care or point of use devices capable of quantitating predictive biomarker(s).

SUMMARY OF THE INVENTION

The present invention relates methods, devices, reagent, systems and kits for the for the detection and diagnosis of ovarian cancer using brain natriuretic peptide (BNP) as a biomarker.

The present invention relates to methods, devices, reagent, systems and kits for monitoring the progression of ovarian cancer and for monitoring the progress of ovarian cancer treatments.

The present invention also relates to quantitative point-of-care devices and methods for the detection of BNP as a diagnostic for ovarian cancer.

In certain embodiments, the present invention provides a method for monitoring BNP for an individual treated with a drug. The method involves obtaining samples from the individual at suitable time points. The samples may be collected at point-of-care or point-of-use by sampling or self-sampling on point-of-care devices or point of use devices, each capable of quantitating the biomarker, or on matrices suitable for storage of at least two samples prior to quantitation of the drug by a central laboratory. The information obtained may be suitable for guiding dosing of the drug for the individual.

The invention also relates to point-of-care and/or point-of-use devices for quantitation BNP which allows for personalized dosing and monitoring for more effective therapies for ovarian cancer.

Samples may be collected by at point-of-care or point of service, e.g., by self-sampling. Samples may be applied to a lateral flow device for quantitation of the drug, and the results transmitted to the physician or physician's agent for pharmacokinetic analysis. In other embodiments, the samples are collected at point-of-care or point-of-service, e.g., by self-sampling, on a suitable storage matrix, e.g., nitrocellulose, prior to delivery of the samples to a central laboratory for quantitation and analysis.

In certain embodiments, samples collected at various times from the individual through point-of-care or point-of-use by self-sampling may be obtained by a central laboratory. The laboratory then tests the samples to quantitate the biomarker of interest and, based on the results, detection or diagnosis of ovarian cancers may be obtained. The results obtained may also be used to determine the magnitude of the diseases' progression as well as to monitor the efficacy of treatment regimens.

In another aspect it provides a kit for biomarker monitoring of an individual treated with a drug. The kit comprises a plurality of point-of-care device or a point of use device capable of quantitating the drug in one or more samples, or matrices suitable for storage of the samples prior to quantitation by a central laboratory.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
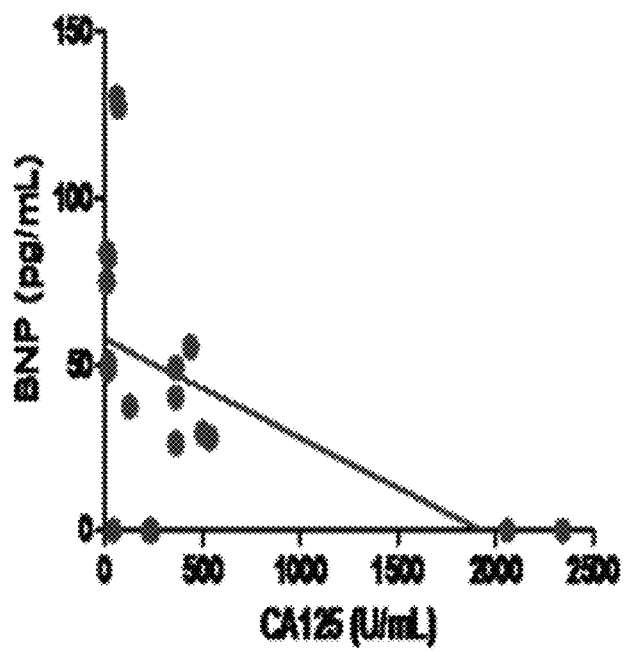
FIGS. 1A-1C are plots of BNP concentration versus CA125 concentration (1A), FSH concentration versus CA125 concentration (1B), and BNP concentration versus FSH concentration (1C).

The present invention relates to methods, devices, reagent, systems and kits for the detection, diagnosis, and progression of ovarian cancer using brain natriuretic peptide (BNP) as a biomarker.

Biomarker data may be obtained from samples collected at point-of-care or point-of-use using for example a lateral flow point of care test. Advantageously, the samples may be obtained by self-sampling. In certain embodiments, the samples may be delivered to a point-of-care device to quantitate the biomarker, and the results thus obtained are reported to the physician or his agent. In one embodiment quantitation of brain natriuretic peptide (BNP) can be monitored using point-of-care and point-of-use detection which allows for personalized dosing and monitoring for more effective therapies for various cancers including ovarian cancers. BNP may be quantitatively detected from various bodily fluids including but not limited to plasma, serum or urine. Point-of-care needs to have an expanded dynamic range of concentration detection. Preferably the assays or test require a single determination with no repeat and no dilution at point-of-care. Most immunoassays have a working range of 2 logs. The methods of the present invention provide for expanding the range of detection for the biomarkers at least one log or at least two logs or at least 3 logs or at least 4 logs or at least 5 logs or at least 6 logs or at least 7 logs or at least 8 logs. For example the assays and tests and methods of the present invention permit an expanded dynamic range of detectable concentrations of BNP. The expanded dynamic range encompasses all possible concentrations of BNP encountered in blood, serum or other bodily fluids. The assays and tests and methods of the present invention also provide cassettes which can be read using an optical reader with 2D barcode capability, and provide that the data can be printed out or stored on the reader for uploading onto a database including but not limited to a clinic, doctor's office or hospital database. The reader utilizes confocal optics with a low distance-to-target ratio. The reflectometric measurement is converted to activity units, using an established calibration curve embedded in the 2D barcode. The cassettes are made such that the samples within are stable for at least 12 or at least 24 or at least 48 or at least 72 hours and thus can be shipped to a central lab or doctor's office for quantitation if the patient does not have access to the reader.

The readers utilized in the present invention include but are not limited to confocal optical readers or cell/smart phone readers. A reflectometric optical reader, which utilizes confocal optics with a low distance-to-target ratio, may be used with the methods, kits and assays of the present inventions. Calculations may be performed in the background using information embedded on the 2D-bar code specific to each lot of cassettes. Alternatively a cell phone reader which provides quantitation at a point-of-care without sufficient resources can be used to capture images of the cassettes and transmit the images over the internet to a facility such as a centralized processing facility where the BNP values can be received in real time.

The present invention provides rapid and quantitative point-of-care testing for BNP including field deployment directly at home or in emergency care situations, and provides for cassettes which can be read directly by the patient or can be shipped to the central lab/doctor's office for reading. As therapeutic drug monitoring (TDM), the test should allow for more effective dosing of the patients and thereby improving effectiveness of treatment. The tests are also patient-centric, inviting better compliance and patient participation in personalizing his/her treatment. The simplicity of the assays would allow for their deployment in underdeveloped regions lacking access to central laboratories with specialized and expensive equipment. The expanded range eliminates the need for dilution of the samples to bring them within working range of the traditional assay.

Alternatively, the samples are collected using a matrix or vessel suitable for collection and storage of the samples until receipt and analysis by a central laboratory. Examples of matrices or vessels suitable for collection and storage of the samples include, but are not limited to, commercially available biological sampling filter paper systems, such as WHATMAN® 3 MM, GF/CM30, GF/QA30, S&S 903, GB002, GB003, or GB004. Several categories of blotting materials for blood specimen collection are available, e.g., S&S 903 cellulose (wood or cotton derived) filter paper and WHATMAN® glass fiber filter paper. The blood spot is placed in one or more designated areas of the filter paper, allowed to dry, and then mailed along with a test request form to the central laboratory. This method of collection has the advantage of obviating the need for collection of samples at a doctor's office or clinic. Thus, multiple samples may be conveniently collected by the patient over a period of 0 to 72 hours at considerable savings of cost and time. This has the advantages of increased efficiency and reduced delays in transmitting results of the analysis to the treating physician, who may use the information to adjust treatment as necessary, and contact the patient to convey the new treatment regimen. In one aspect, one or more biomarkers are provided for use either alone or in various combinations to diagnose ovarian cancer, permit differential diagnosis of pelvic masses as benign or malignant, monitor ovarian cancer progression or monitor ovarian cancer recurrence.

Any of the biomarkers described herein may be used in a variety of clinical indications for ovarian cancer, including any of the following: detection of ovarian cancer, characterizing ovarian cancer (e.g., determining ovarian cancer type, sub-type or stage), such as by determining whether a pelvic mass is benign or malignant; determining ovarian cancer prognosis; monitoring ovarian cancer progression or remission; monitoring for ovarian cancer recurrence; monitoring metastasis; treatment selection (e.g., pre- or post-operative chemotherapy selection; monitoring response to a therapeutic agent or other treatment, combining biomarker testing with additional biomedical information.

As an example of the manner in which the biomarker described herein may be used to diagnose ovarian cancer, differential expression of one or more of the biomarkers described herein in an individual who is not known to have ovarian cancer may indicate that the individual has ovarian cancer thereby enabling detection of ovarian cancer at an early stage of the disease when treatment is most effective. Decreased expression of the biomarker from "normal" during the course of ovarian cancer may be indicative of ovarian cancer progression whereas an increase in the expression as compared with normal expression may indicate that the individual is in remission or is being successfully treated. Decreases in the degree of biomarker expression as compared to "normal" may indicate cancer progression or ineffectiveness of ovarian cancer treatment. Additionally a decrease in the differential expression of one or more of the biomarkers after an individual has apparently been cured of ovarian cancer may be indicative or ovarian cancer recurrence. In this case, cancer treatment may be resumed or current treatment may be augmented or supplemented as need be. In addition, a differential change in the level of biomarker might also be indicative of an individual's response to a particular therapeutic agent. Differential expression refers to expression of a biomarker that is activated to a higher or lower level in a subject suffering from a specific disease, relative to its expression in a normal or control subject or a subject who does not have the specific disease. Differential expression includes both quantitative and qualitative differences in expression among normal and diseased cells or among cells which have undergone different disease events or different treatments.

The biomarker of the present invention is brain natriuretic peptide (BNP). Brain natriuretic peptide is a 32 amino acid, approximately 3 kDa peptide that is encoded by the human NPPB gene and plays a role in the modulation of diuresis, vasorelaxation, and secretion of renin and aldosterone.

The BNP biomarker may be used in combination with one or more other biomarkers for ovarian cancer or other diseases or conditions (e.g., other cancers). Thus, the BNP biomarker can be used as a biomarker in a biomarker panel.

The BNP biomarker may be differentially expressed at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100%. The level of expression of the biomarker of the present invention may be between about 10% lower to about 100% lower or about 10% lower to about 90% lower or about 10% lower to about 80% lower or about 10% lower to about 70% lower or from about 10% lower to about 60% lower or from about 10% lower to about 50% lower or from about 10% lower to about 40% lower or from about 10% lower to about 30% lower or about 10% lower to about 20% lower or about 20% lower to about 100% lower or about 20% lower to about 90% lower or from about 20% lower to about 80% lower or from about 20% lower to about 70% lower or from about 20% lower to about 60% lower or from about 20% lower to about 50% lower or from about 20% lower to about 40% lower or from about 20% lower to about 30% lower or from about 50% lower to about 100% lower than normal or than that of a control.

The biomarker is preferably differentially present at a level that is statistically significant (e.g. a p-value less that 0.05 and/or a q-value of less than 0.10 as determined by either Welch's T-test or Wilcoxon's rank-sum test). Alternatively, the biomarker demonstrates a correlation with the presence of ovarian cancer or particular stages of ovarian cancer. The range of correlations is between negative 1 (−1), a perfect negative correlation, and positive 1 (+1), a perfect positive correlation. Zero (0) would mean no correlation. A substantial positive correlation refers to a biomarker having a correlation between +0.25 and +1.0 with a disease or clinical measurement while a substantial negative correlation refers to a biomarker having a correlation between −0.25 and −1.0 with a disease or clinical measurement. A significant positive correlation refers to a biomarker having a correlation between +0.25 and +1.0 with a disease or clinical measurement while a significant negative correlation refers to a biomarker having a correlation between −0.25 and −1.0 with a disease or clinical measurement.

In some cases it will be desirable to establish normal or baseline values (or ranges) for biomarker expression levels. Normal levels can be determined for any particular population, subpopulation or group according to standard methods known to those of skill in the art. Generally baseline (normal) levels of biomarkers are determined by quantifying the amount of biomarker in biological samples (e.g., fluids, cells or tissues) obtained from normal (healthy) individuals. Application of standard statistical methods permits determination of baseline levels of expression as well as deviations from such baseline levels.

A biomarker value can be detected by using any of a variety of known analytical methods. Biomarker detection may be facilitated by the use of a capture agent which is one or more molecules which can specifically bind the biomarker. The capture agent, in solution or immobilized on a solid support, may be exposed to the biomarker and binding may be detected in a variety of ways including, but not limited to, fluorescence, chemiluminescence, dyes, and other optically detectable means. Immunoassay methods are based on the binding of an antibody to its corresponding analyte (e.g., BNP) and can detect the analyte in a sample depending on the specific assay format.

According to the American Cancer Society ovarian cancer can be staged according to the AJCC/TNM System. This describes the extent of the primary tumor (T), the absence or presence of metastasis to nearby lymph nodes (N), and the absence or presence of distant metastasis (M). T categories for ovarian cancer include: T1: the cancer is confined to one or both ovaries; T2: the cancer is in one or both ovaries and is extending into pelvic tissues; and T3: the cancer is in one or both ovaries and has spread to peritoneum. N categories indicate if the cancer has spread to regional (nearby) lymph nodes. Nx: no description of lymph node involvement is possible because information is incomplete. N0: no lymph node involvement. N1: cancer cells are found in the lymph nodes close to tumor. Once a patient's T, N, and M categories have been determined, this information is combined in a process called stage grouping to determine the stage, expressed in Roman numerals from stage I (the least advanced stage) to stage IV (the most advanced stage). Stage 1: the cancer is still contained within the ovary (or ovaries). It has not spread outside the ovary. Stage 2: the cancer is in one or both ovaries and has spread to other organs (such as the uterus, fallopian tubes, bladder, the sigmoid colon, or the rectum) within the pelvis. It has not spread to lymph nodes, the peritoneum, or distant sites. Stage 3: the cancer is in one or both ovaries, and one or both of the following are present: (1) cancer has spread beyond the pelvis to the lining of the abdomen; (2) cancer has spread to lymph nodes. Stage 4: the most advanced stage of ovarian cancer; in this stage the cancer has spread to the inside of the liver, the lungs, or other organs located outside the peritoneal cavity. Finding ovarian cancer cells in the fluid around the lungs is also evidence of stage IV disease.

Non-limiting examples of suitable devices or methods of testing drugs include lateral flow devices for the determination of the concentration of an analyte in a sample comprising providing a lateral flow strip for use in measuring the analyte. Examples of analytes that may be tested include therapeutic drugs, drug metabolites, and hormones. Application of the sample to the lateral flow strip causes a fraction of the analyte in the sample to bind to a component of the lateral flow strip such that a detectable signal proportional to the concentration of the analyte in the sample is produced.

Alternatively, the quantitation may be conducted on samples submitted by individuals to a laboratory by any suitable assay, including, but not limited to, those currently known to the art, such as ELISA, liquid chromatography-mass spectrometry (LC-MS), thin layer chromatography (TLC), high-performance liquid chromatography (HPLC), and mass spectrometry (MS) or other traditional assays for drug monitoring at central lab have been well illustrated. The samples could be whole blood collected following a finger prick on a suitable matrix and stored as a dry blood spot that is shipped or otherwise delivered to a laboratory for testing. Sampling can be performed with capillary and/or device designed to deliver precise and small amount of blood to the dried blood spot card-card punch variability replaced pipette variability.

The following examples are provide for the purpose of illustrating, not limiting the invention.

Example 1

Measurement of LH, FSH, and BNP Levels

Serum samples collected at time of diagnosis of ovarian cancer were tested using rapid and quantitative point-of-care (POC) devices for blood biomarkers (LH, FSH, and BNP) and the data was evaluated using JMP9 statistical analysis software. Quantitative lateral flow assays for FSH and LH were performed according to Larn Hwang, Chao Hsiao, Kouros Motamed, Vuong Trieu (2012) Rapid and Quantitative Lateral Flow Point-of-Care Therapeutic Drug Monitoring (TDM) Assays for LH and FSH. American Association for Cancer Research (AACR) Annual Meeting, Mar. 31-Apr. 4, 2012. Quantitative BNP assay was from Humasis (Korea). FSH range=5-10,000 IU/L; LH range=1-1,700 IU/L; BNP range=25-800 pg/mL.

TABLE 1

| BNP (pg/mL) Quartiles | 10% | 25% | median | 75% | 95% |
|---|---|---|---|---|---|
| Normal | 0 | 0 | 0 | 84.1 | 177.3 |
| Ovarian Cancer | 0 | 0 | 40.0 | 74.8 | 127.3 | p = 0.02, chi-square

TABLE 2

| LH (pg/mL) Quartiles | 10% | 25% | median | 75% | 95% |
|---|---|---|---|---|---|
| Normal | 4.83 | 6.00 | 16.65 | 62.53 | 83.72 |
| Ovarian Cancer | 4.50 | 12.60 | 17.40 | 40.00 | 61.20 | p = 0.9817 Wilcoxon statistics

TABLE 3

| BNP (pg/mL) Quartiles | 10% | 25% | median | 75% | 95% |
|---|---|---|---|---|---|
| Normal | 3.79 | 7.75 | 13.40 | 99.68 | 828.84 |
| Ovarian Cancer | 15.10 | 74.30 | 151.60 | 418.60 | 825.00 | p = 0.0102 Wilcoxon statistics

In the serous adenocarcinoma group, FSH level was higher (median=151.6 mU/ml) vs. normal controls (median of 13.4 mU/ml, p=0.01, Wilcoxon). Moreover, incidence of BNP>25 pg/ml was higher for patients (14 of 19, 74%) vs. normal controls (3 of 10, 30%, p=0.02, Chi-square). FSH progressively increased from normal controls, to normotensive patients, to hypertensive patients with median FSH values of 13.4, 79.3, and 232.2, respectively. The same was not observed for BNP. FSH increase in hypertensive patients was not accompanied by increase in BNP. However, incidence of BNP>25 pg/ml was higher for patients (14 of 19, 74%) vs. normal controls (3 of 10, 30%, p=0.02, Chi-square). No differences were observed for LH. These data suggest the BNP and FSH hormones play a role(s) in ovarian cancer.

Figure 1B:
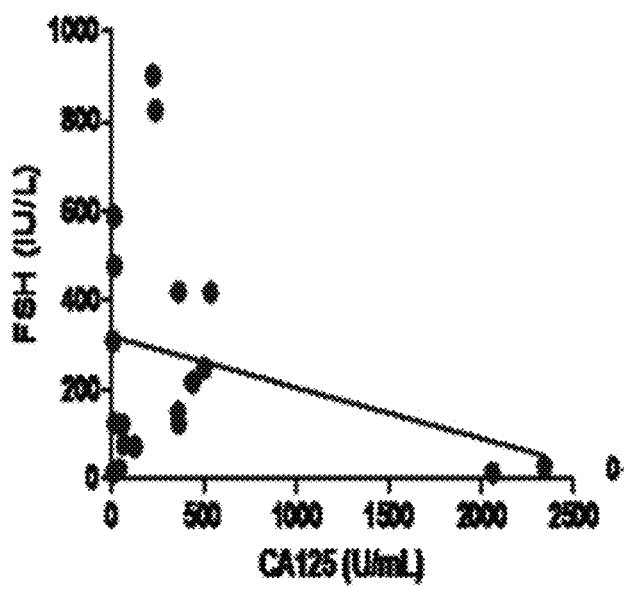
Figure 1C:
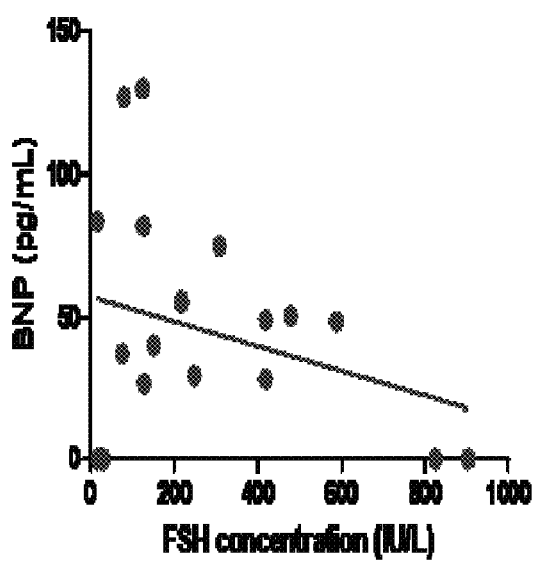
Figure 2A:
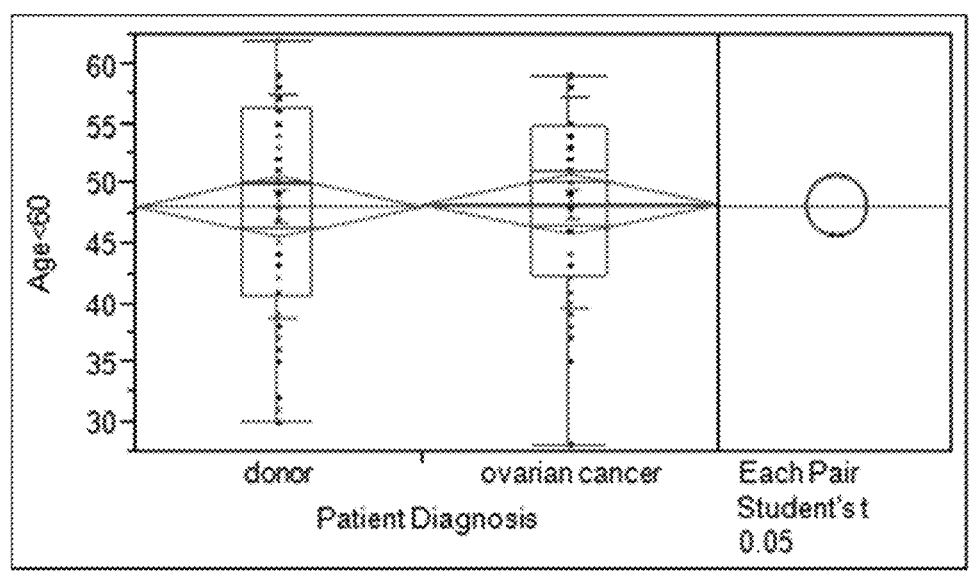
FIGS. 2A-2D are plots of age matched (2A) (donor 50 yr; ovarian cancer patient 51 yr), height matched (2B) (donor 166 cm; ovarian cancer patient 165 cm), body mass index (BMI) (2C) (donor 25; ovarian cancer patient 27), and weight matched (2D) (donor 70 kg; ovarian cancer patient 72 kg) donors and ovarian cancer patients.
Figure 2B:
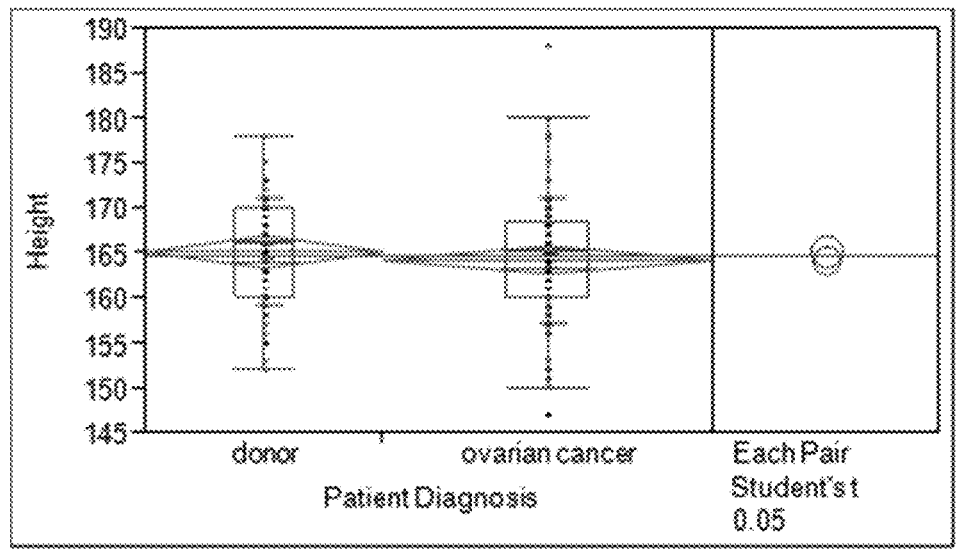
Figure 2C:
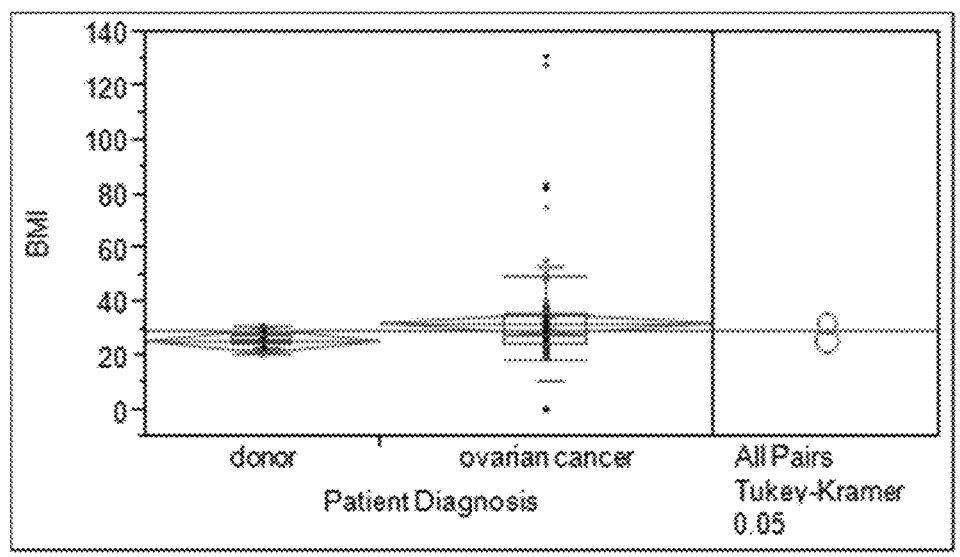
Figure 2D:
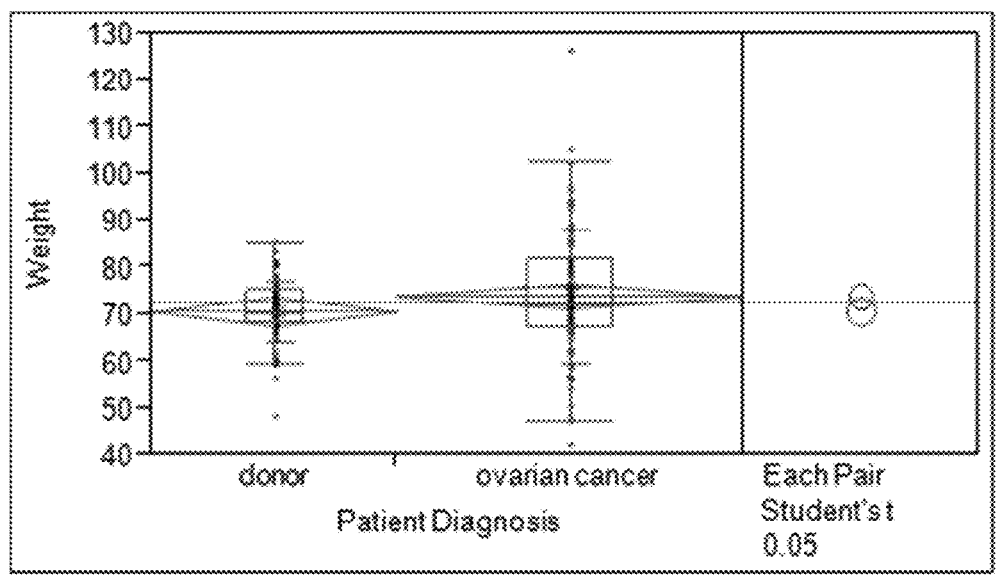

There were no correlations between CA125 and FSH or BNP suggesting that they are independent biomarkers (see FIGS. 1A-1C). FSH and BNP exhibited increased incidence/level among cancer patients versus age matched normal. FSH is probably acting as regulator of cancer cell expression as well as induction of angiogenesis. Elevated levels of FSH are shown in FIG. 1B. The role of BNP is unknown at the moment. The data shown in this example demonstrated the use of POC/POU device for monitoring the relevant blood biomarkers (FSH, LH, hCG, and BNP). The association of BNP with ovarian cancer was previously unrecognized.

Example 2

Measurement of BNP Levels in Ovarian Cancer Patients

Figure 3:
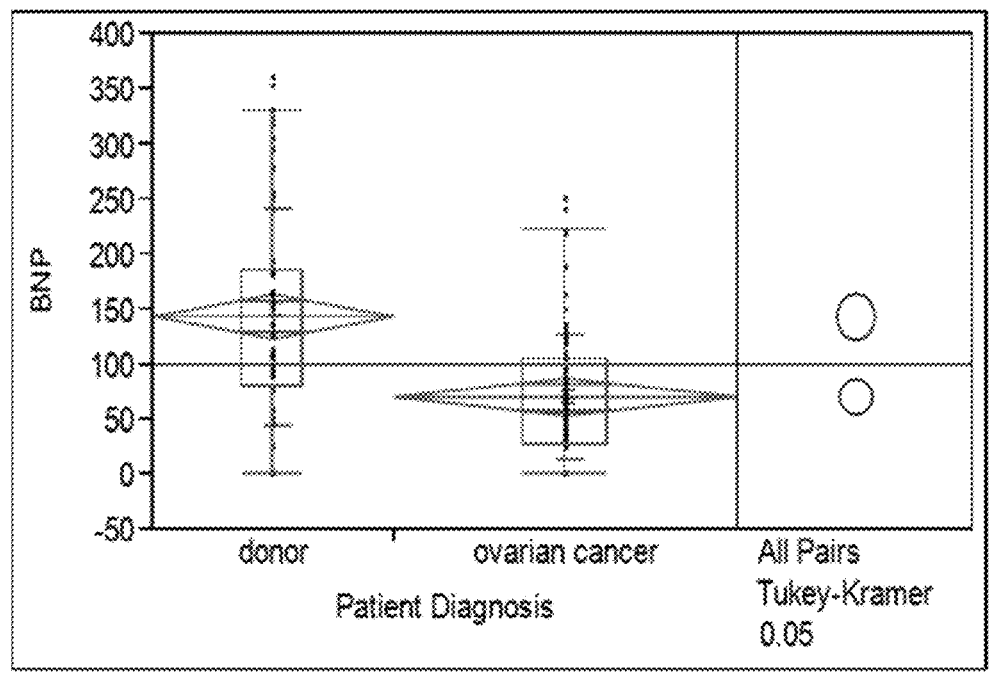
FIG. 3 is a plot of the BNP levels (ng/mL) of ovarian cancer patients and donors (t Test Prob>F<0.0001) (donor 126.35 ng/mL; ovarian cancer patient 55.34 ng/mL).

BNP levels were determined for 55 donors and 79 ovarian cancer patients. The donors and ovarian cancer patients were matched for age (donor 50 years; patient 51 years), height (donor 166 cm; patient 165 cm), weight (donor 70 kg; patient 72 kg) and BMI (donor 25; patient 27) as seen in FIGS. 2A-2D. The donor average BNP was 126.36 ng/mL, whereas the average BNP level for the patients was 55.34 ng/mL. FIG. 3 shows a plot of the data.

Figure 4A:
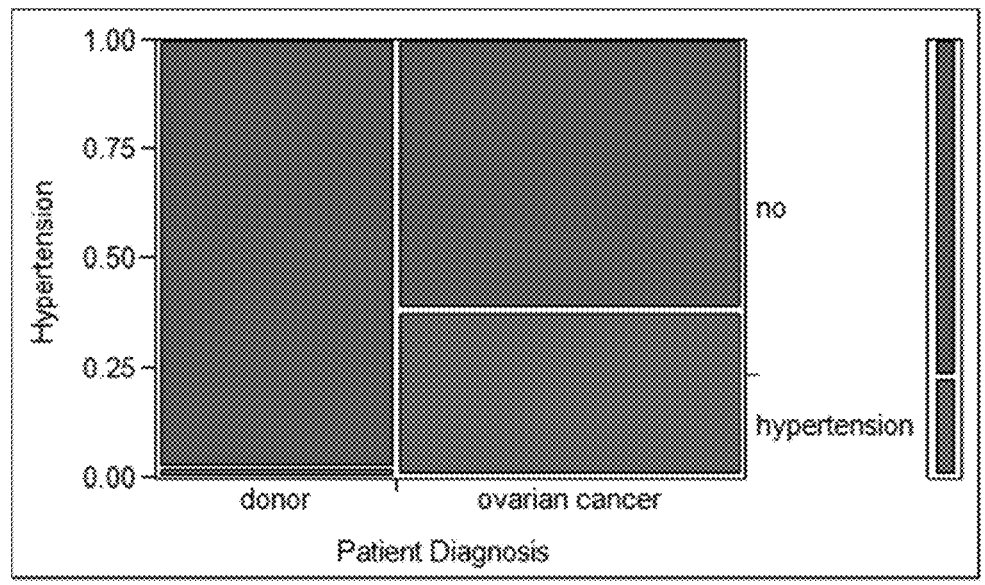
FIG. 4A is a bar graph of number of patients (79) and donors (55) with hypertension (patients with hypertension 30; donors with hypertension 1) and without hypertension (patients without hypertension 49; donors without hypertension 54).
Figure 4B:
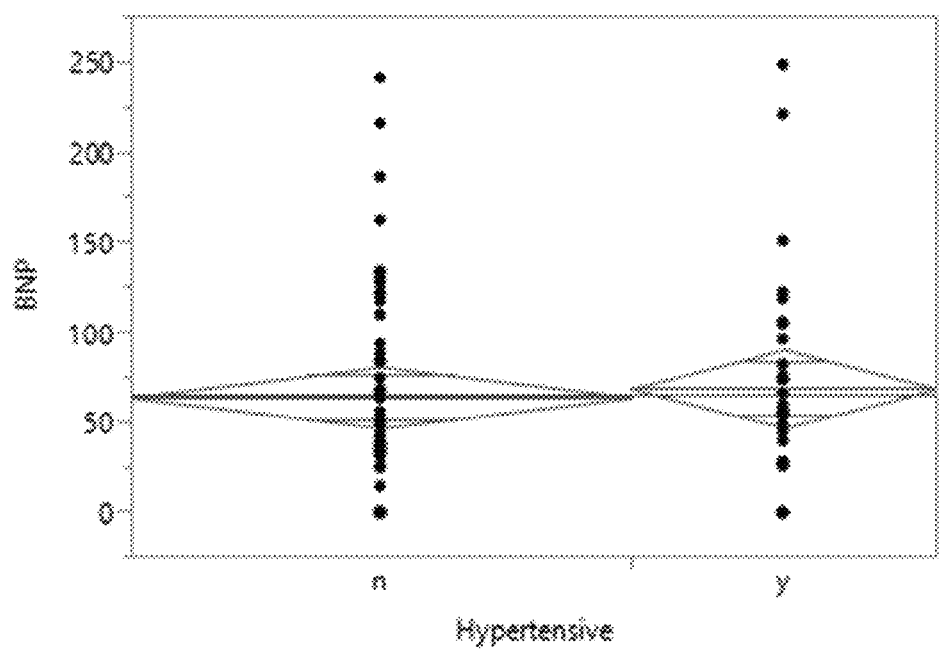
FIG. 4B is a plot of BNP levels in ovarian cancer patients with hypertension (Y) (30 patients; mean 68.9423) and without hypertension (N) (49 patients; mean 64.0855) (t Test Prob>F<0.7269).
Figure 5:
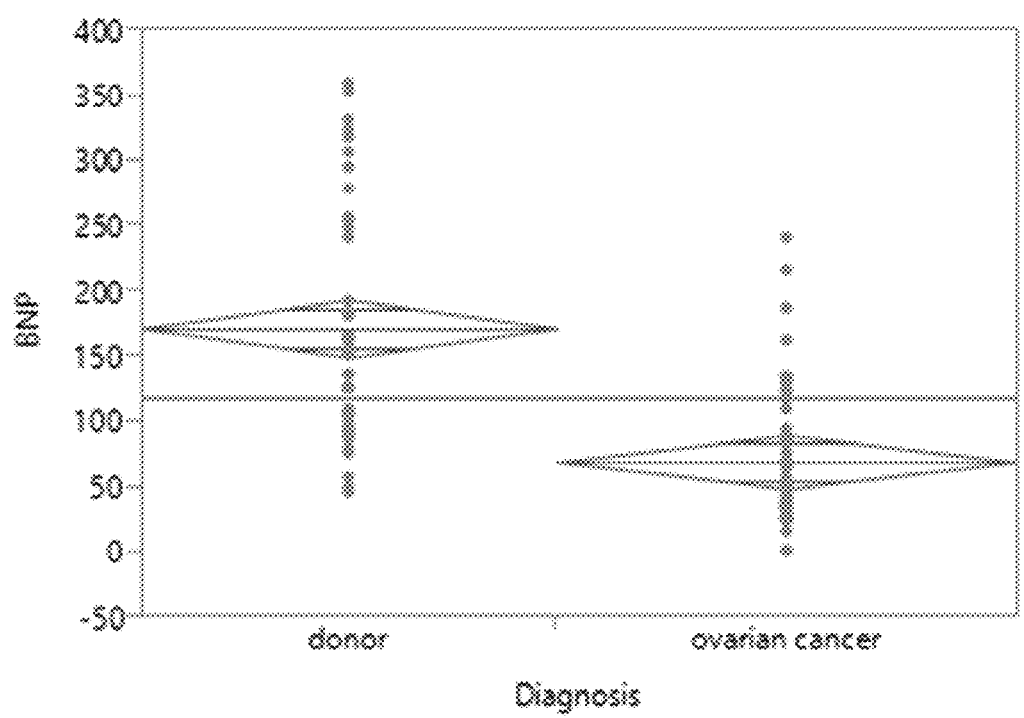
FIG. 5 is a plot of BNP levels in ovarian cancer patients (49 patients; mean 68.881) and donors (44 donors; mean 171.066) who are normotensive (t Test Prob>F<0.0001).

As the ovarian cancer population was imbalanced for hypertension, a subgroup analysis was performed. Of the 55 donors one had hypertension and in the patient group 30 had hypertension and 49 were normotensive (FIG. 4A). The hypertensive and normotensive patients were compared (FIG. 4B) and the mean BNP level for the hypertensive patients was 68.9423 ng/mL and the mean BNP level for the normotensive patients was 64.0855 ng/mL. The normotensive patients were compared to normotensive donors (FIG. 5). The mean BNP level for the normotensive patients was 68.881 ng/mL and the mean BNP level for the normotensive donors was 171.066 ng/mL. Thus, there is lower BNP in normotensive cancer patients versus normotensive donors.

BNP level is depressed in ovarian cancer patients and there appears to be little to no differences between hypertensive patients versus normotensive patients with respect to BNP levels of those with ovarian cancer. BNP level remained depressed when normotensive patients were compared to normotensive donors. This is the first demonstration of a linkage between ovarian cancer and the cardiovascular system.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Further advantages of the methods of the present invention can be achieved by those skilled in the art based upon the embodiments described herein and are thus specifically within the scope of the present invention.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for monitoring the efficacy of an anti-ovarian cancer treatment in a patient diagnosed with ovarian cancer and treating the patient, comprising:

measuring, with a quantitative lateral flow device, a level of brain natriuretic peptide (BNP) in the patient's serum or plasma obtained at a first point in time, wherein the level at the first point in time is less than 68.9 ng/mL serum or plasma;

treating the patient with the anti-ovarian cancer treatment;

measuring, with a quantitative lateral flow device, the level of BNP in the patient's serum or plasma obtained at a second point in time;

comparing the level of BNP in the subject at the first point in time with the level at the second point in time to determine the efficacy of the ovarian cancer treatment;

indicating an ineffective treatment where there is no increase or a decrease in the level of BNP at the second point in time compared to the level of BNP at the first point in time; and treating the patient with a different anti-ovarian cancer drug.

* * * * *